(12) United States Patent
Mason et al.

(10) Patent No.: US 7,326,323 B2
(45) Date of Patent: Feb. 5, 2008

(54) HIGH CAPACITY PURIFICATION OF THERMALLY UNSTABLE COMPOUNDS

(75) Inventors: Robert Michael Mason, Houston, TX (US); Jeffery Alan Goodwin, League City, TX (US); Ronald Drew Myers, Southampton, PA (US); Michael Stanley DeCourcy, Houston, TX (US)

(73) Assignee: Rohm and Haas Company, Philadelphia, PA (US)

( * ) Notice: Subject to any disclaimer, the term of this patent is extended or adjusted under 35 U.S.C. 154(b) by 70 days.

(21) Appl. No.: 11/211,222

(22) Filed: Aug. 25, 2005

(65) Prior Publication Data

US 2006/0000703 A1    Jan. 5, 2006

Related U.S. Application Data

(62) Division of application No. 10/307,960, filed on Dec. 3, 2002, now abandoned.

(51) Int. Cl.
  *B01D 3/42* (2006.01)
  *C07C 51/44* (2006.01)
  *C07C 53/08* (2006.01)

(52) U.S. Cl. .............. 203/1; 203/91; 203/DIG. 21; 562/600; 562/608

(58) Field of Classification Search .......... 203/1, 203/91, DIG. 21, 100; 562/600, 607, 608
  See application file for complete search history.

(56) References Cited

U.S. PATENT DOCUMENTS

| | | | |
|---|---|---|---|
| 3,798,264 A | 3/1974 | Kubota et al. ............ 260/526 |
| 3,859,175 A * | 1/1975 | Ohrui et al. ............... 203/46 |
| 3,988,213 A | 10/1976 | Yoshida et al. ............ 203/9 |
| 4,021,310 A | 5/1977 | Shimizu et al. ............ 203/8 |
| 4,156,633 A * | 5/1979 | Horlenko et al. .......... 203/93 |
| 4,177,110 A | 12/1979 | Watson ..................... 203/9 |
| 4,422,903 A | 12/1983 | Messick et al. |
| 4,483,747 A * | 11/1984 | Aruga et al. .............. 203/92 |
| 5,045,233 A | 9/1991 | Kita et al. ................ 252/399 |
| 5,315,037 A | 5/1994 | Sakamoto et al. ........ 562/345 |
| 5,554,329 A | 9/1996 | Monkelbaan et al. |
| 5,785,821 A | 7/1998 | Sakamoto et al. ......... 203/57 |
| 5,817,865 A | 10/1998 | Machhammer et al. ... 560/208 |
| 5,831,124 A | 11/1998 | Machhammer et al. ... 562/600 |

(Continued)

FOREIGN PATENT DOCUMENTS

DE    196 27 847    1/1998

(Continued)

OTHER PUBLICATIONS

Henry Z. Kister, C.F. Braun, Inc., *Distillation Operation*, McGraw-Hill, Inc., pp. 201-203.

(Continued)

*Primary Examiner*—Virginia Manoharan
(74) *Attorney, Agent, or Firm*—Marcella M. Bodner

(57) ABSTRACT

Separations processes and apparati capable of purifying thermally sensitive materials at high capacity. An apparatus having a rectification section and a stripping section with the stripping section having a stripping tray with 5 to 50% open area, a pressure drop from 0.02 psi to 0.2 psi and a tray efficiency during operation of the column which is equal to or greater than 20%.

4 Claims, 4 Drawing Sheets

DUAL-COLUMN DESIGN

U.S. PATENT DOCUMENTS

| | | | |
|---|---|---|---|
| 5,910,607 A | 6/1999 | Sakakura et al. | 562/532 |
| 5,929,285 A | 7/1999 | Chikamori et al. | 568/372 |
| 5,961,790 A | 10/1999 | Herbst et al. | 203/59 |
| 6,084,127 A | 7/2000 | Sakamoto et al. | 562/600 |
| 6,096,920 A | 8/2000 | Allen et al. | 562/406 |
| 6,123,812 A | 9/2000 | Bessling et al. | 203/2 |
| 6,128,922 A | 10/2000 | Dean et al. | 62/643 |
| 6,149,136 A | 11/2000 | Armstrong et al. | 261/19 |
| 6,180,827 B1 * | 1/2001 | Lee et al. | 562/600 |
| 6,214,174 B1 | 4/2001 | Matsumoto et al. | 203/100 |
| 6,263,701 B1 | 7/2001 | Herron et al. | 62/646 |
| 6,264,800 B1 | 7/2001 | Gupta | 203/96 |
| 6,350,351 B1 | 2/2002 | Popov et al. | 202/158 |
| 6,365,006 B1 | 4/2002 | Aristovich et al. | 203/98 |
| 6,390,454 B1 | 5/2002 | Urbanski et al. | 261/114.1 |
| 6,395,140 B1 | 5/2002 | Herbst et al. | |
| 6,399,817 B1 | 6/2002 | Chapman et al. | |
| 6,407,287 B2 | 6/2002 | Matsumoto et al. | 562/532 |
| 6,414,183 B1 | 7/2002 | Sakamoto et al. | 560/218 |
| 6,465,665 B1 | 10/2002 | Schersl | 552/545 |
| 6,475,349 B1 | 11/2002 | McKeigue et al. | 203/100 |
| 6,478,930 B2 | 11/2002 | Gupta | 203/96 |
| 6,479,689 B1 | 11/2002 | Tojo et al. | 558/277 |
| 6,483,000 B2 | 11/2002 | Becker | 585/800 |
| 6,641,700 B1 | 11/2003 | Matsumoto et al. | |
| 6,755,943 B1 | 6/2004 | Mizutani et al. | |
| 2001/0016668 A1 | 8/2001 | Mitsumoto et al. | |
| 2003/0111331 A1 | 6/2003 | Chalfant et al. | |

FOREIGN PATENT DOCUMENTS

| | | |
|---|---|---|
| DE | 19627850 | 1/1998 |
| DE | 19634614 | 3/1998 |
| DE | 198 27 087 | 2/1999 |
| DE | 197 46 688 | 4/1999 |
| DE | 197 46 690 | 4/1999 |
| DE | 199 17 967 | 11/1999 |
| DE | 199 07 316 | 8/2000 |
| DE | 199 11 405 | 9/2000 |
| DE | 197 46 689 | 5/2002 |
| DE | 198 14 449 | 10/2002 |
| EP | 778255 A1 | 6/1997 |
| EP | 861820 A | 9/1998 |
| EP | 0 937 488 A2 | 8/1999 |
| EP | 1070 700 A2 | 1/2000 |
| EP | 0989109 | 3/2000 |
| EP | 0 990 636 A1 | 4/2000 |
| EP | 1 029 573 A2 | 8/2000 |
| EP | 1029572 A2 | 8/2000 |
| EP | 1 035 103 A2 | 9/2000 |
| EP | 1034824 A | 9/2000 |
| EP | 1035102 (A1) | 9/2000 |
| EP | 1041062 | 10/2000 |
| EP | 1043050 | 10/2000 |
| EP | 1043050 A2 | 10/2000 |
| EP | 1044957 A | 10/2000 |
| EP | 1 029 573 A3 | 11/2000 |
| EP | 1053995 | 11/2000 |
| EP | 1 065 197 A1 | 1/2001 |
| EP | 1070 700 A2 | 1/2001 |
| EP | 1084740 | 3/2001 |
| EP | 1095685 | 5/2001 |
| EP | 1097741 | 5/2001 |
| EP | 1097742 A | 5/2001 |
| EP | 1 106 598 A2 | 6/2001 |
| EP | 0765854 B1 | 4/2002 |
| GB | 1127127 | 9/1968 |
| JP | 2000239228 | 9/2000 |
| WO | WO 9748669 | 12/1997 |
| WO | WO 01/01668 A1 | 1/2001 |
| ZA | 200101898 A | 5/2001 |

OTHER PUBLICATIONS

Henry Z. Kister, Brown & Root Braun, Alhambra, CA, *Distillation Design*, pp. 313 and 350.

Henry Z. Kister, Brown & Root Braun, Alhambra, CA, *Distillation Design*, pp. 382-395 McGraw-Hill, 1992.

Henry Z. Kister, Brown & Root Braun, "Tray Design and Operation", Chapter 6, pp. 259, 260, 266, 267, 309-317 and 350.

Henry Z. Kister, C.F. Braun, Inc., *Distillation Operation*, McGraw-Hill, Inc., pp. 201-203, 1990.

Henry Z. Kister, Brown & Root Braun, Alhambra, CA, *Distillation Design*, pp. 313 and 350, 1992.

Henry Z. Kister, Brown & Root Braun, Alhambra, CA, *Distillation Design*, pp. 382-395 McGraw-Hill, 1992.

Henry Z. Kister, Brown & Root Braun, "Tray Design and Operation", Chapter 6, pp. 259, 260, 266, 267, 309-317 and 350, 1992.

* cited by examiner

FIG. 1: SINGLE COLUMN DESIGN
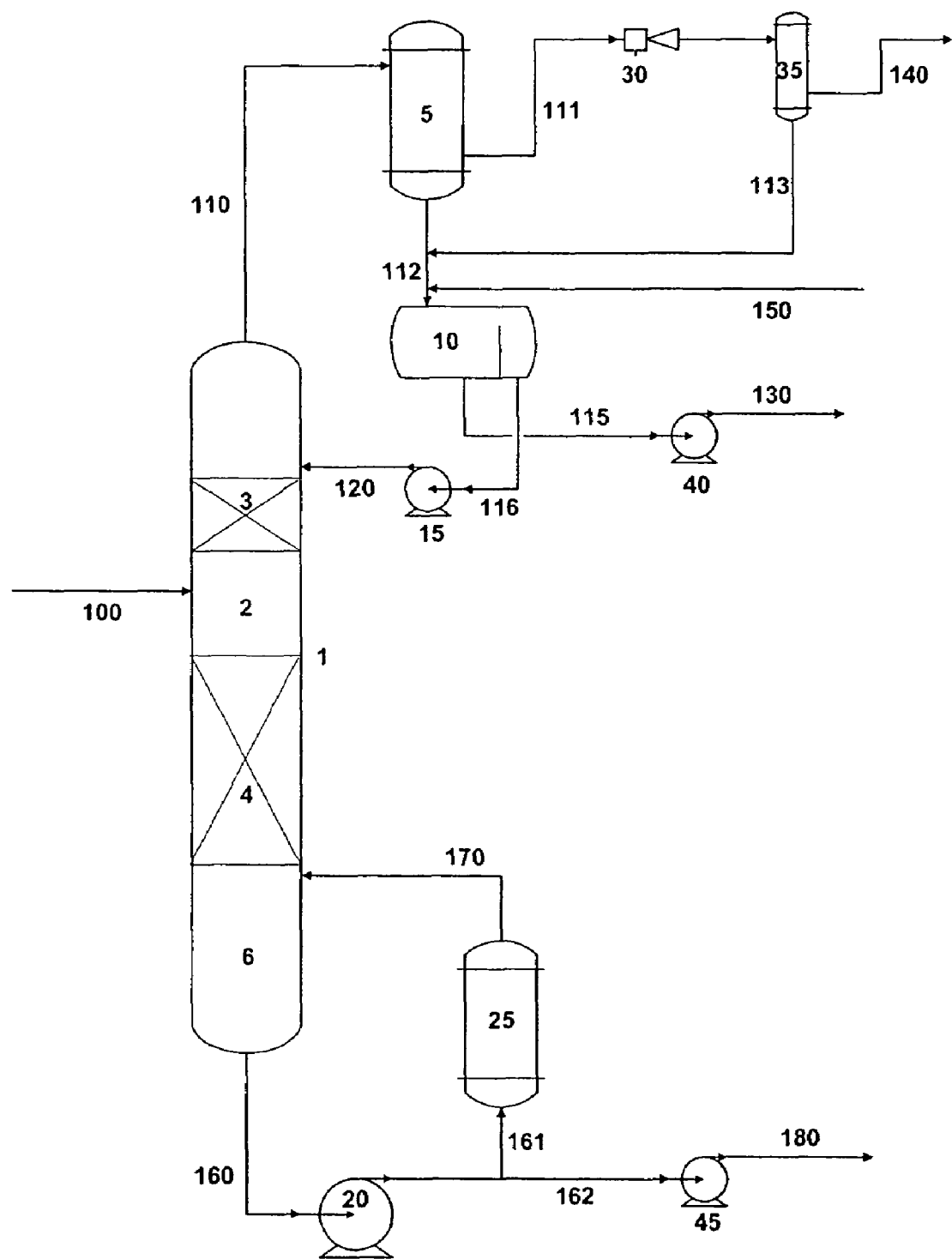

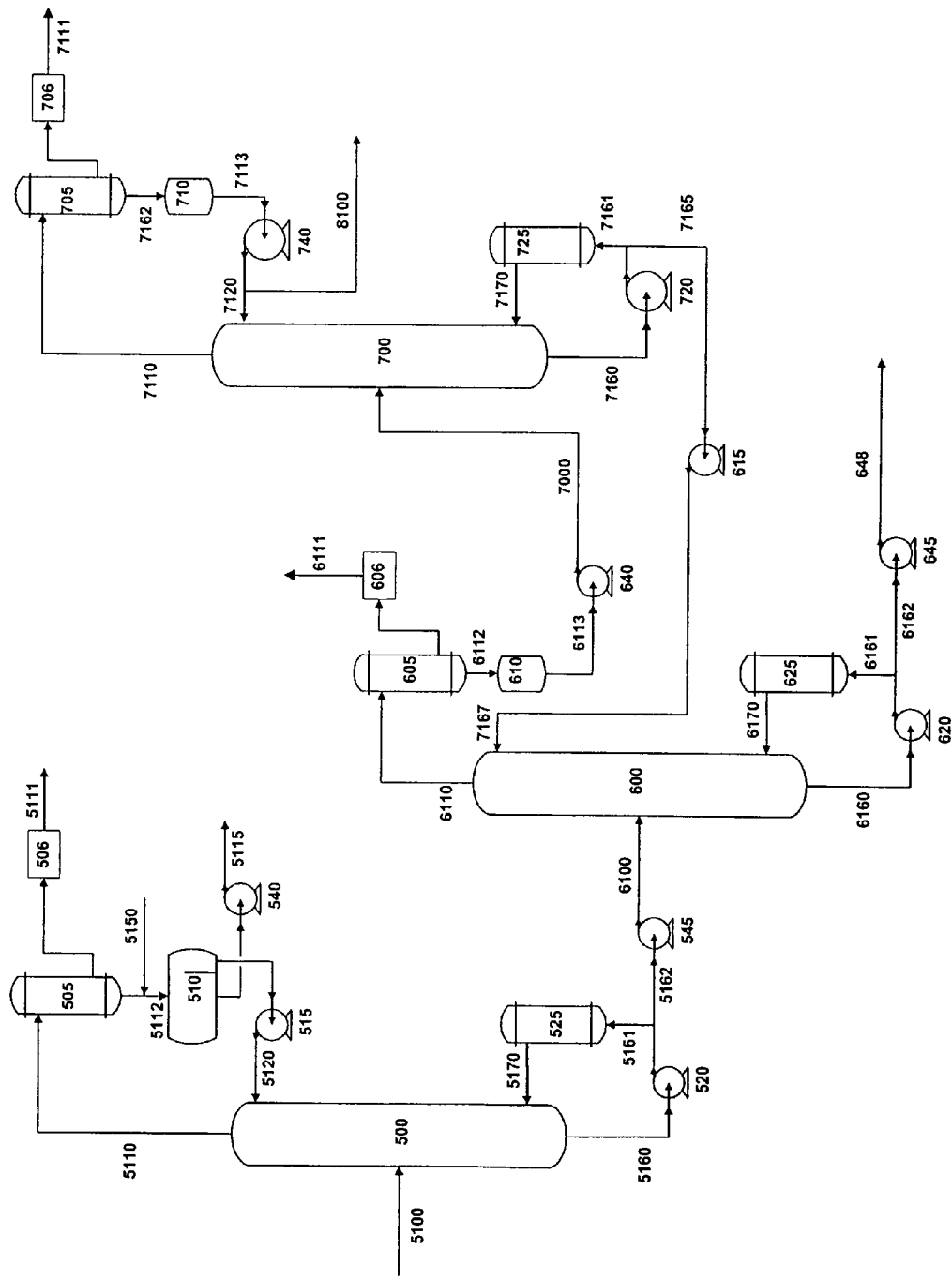
FIG. 2: DUAL-COLUMN DESIGN

FIG. 3: DISTILLATION TRAY
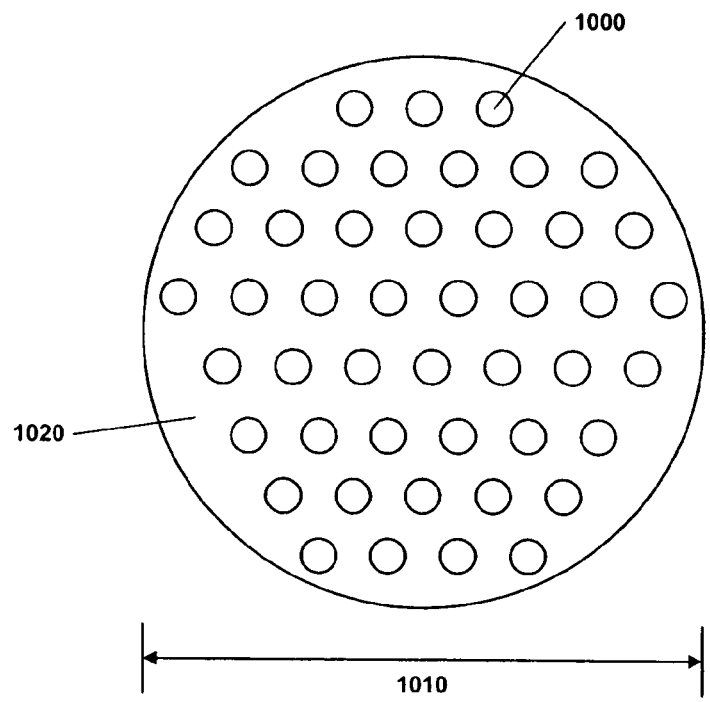
FIG. 4: TRAY HYDRAULICS
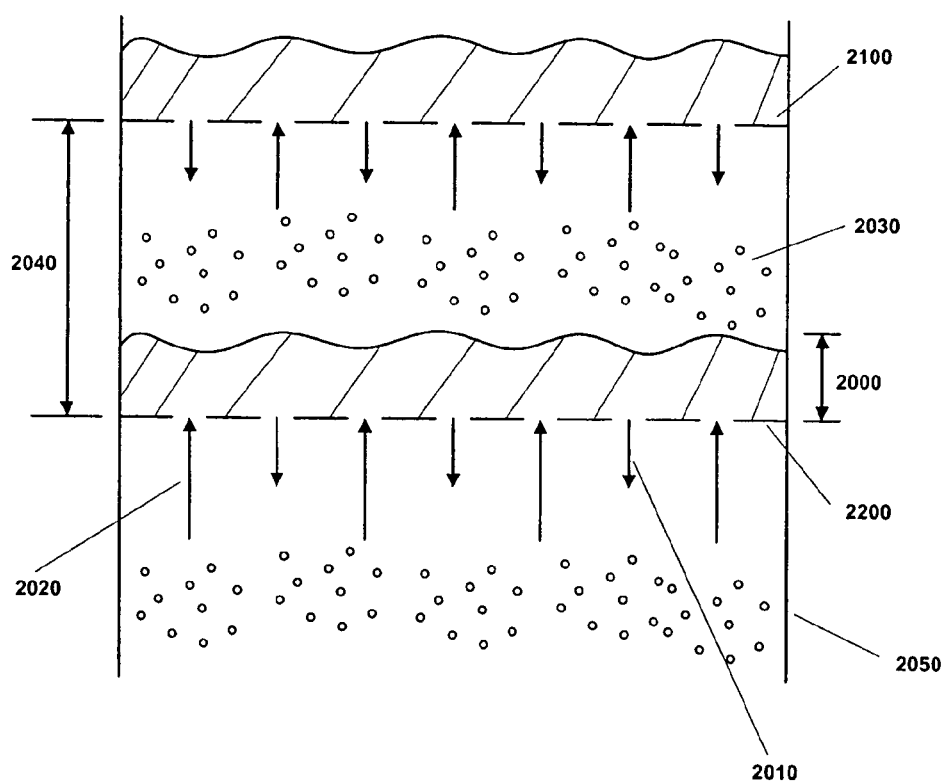

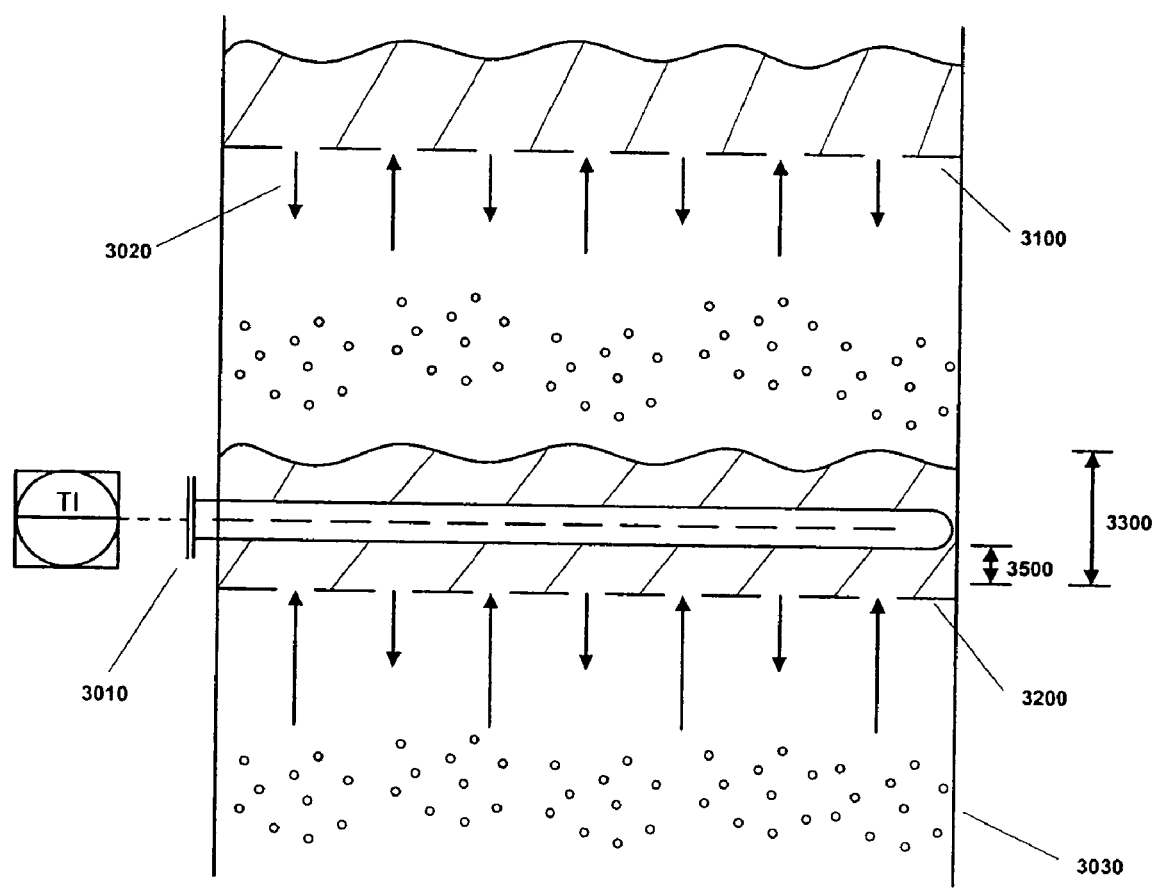
FIG. 5: TEMPERATURE CONTROL

HIGH CAPACITY PURIFICATION OF THERMALLY UNSTABLE COMPOUNDS

This non-provisional application is a divisional of non-provisional U.S. patent application Ser. No. 10/307,960, filed Dec. 3, 2002, now abandoned, priority benefit of which is claimed under 35 U.S.C. §120.

FIELD OF THE INVENTION

This invention is related to the methods and apparati for the high capacity purification of thermally sensitive, unstable, or reactive compounds.

BACKGROUND OF THE INVENTION

The purification of thermally sensitive, unstable, or reactive compounds such as acrylic acid is typically attempted by continuous vacuum distillation or other vapor-liquid separation processes utilizing low pressure drop trays.

The known distillation columns (column(s)) commonly employed in the separation of thermally unstable and reactive compounds experience hydraulic instability, oscillation and unpredictable behavior. Column trays run dry or have dry spots. These columns and trays experience polymer deposition, fluid bypassing, poor hydraulics, poor mixing, flow channeling and flow maldistribution, liquid weeping and poor liquid-vapor interaction. Any one, or a combination, of these factors can result in reduced tray efficiencies and poor column performance.

The presence of polymer in separations processes is a significant problem. Polymer can be present or accumulate on column trays, or anywhere throughout the column. Vapor phase condensation, or liquid-phase polymerization has an equal chance of seeding on any internal column surface. Large gradients in polymer volume may be seen across or down a column's physical profile. Polymer may migrate throughout the column and associated equipment. As a result stream strainers and pumps plug with polymer. The columns must be frequently cleaned. Maintenance and personnel costs are burdensome and run times are short.

In traditional distillation processes for thermally sensitive materials, high temperatures and/or high per tray pressure drops have been determined to increase unwanted polymerization and create production difficulties including loss of efficiency, reduced capacity, damage to equipment, high maintenance and increased energy costs. Inhibitors can be employed to reduce polymerization, however the cost of inhibitors is significant and reduces product purity. In view of these problems, it is common for manufacturers to employ smaller diameter columns or multiple columns. Such approaches are burdensome to operate and expensive to build.

The aforementioned hydraulic and polymer based problems lower tray and column efficiency and prevent separations processes from meeting purity specifications. They also create process control difficulties, result in unreliable sensor data and prevent accurate process simulation.

The purification processes utilized by manufacturers of acrylic acid (an industrially important compound which is reactive and thermally unstable) experience problems including, but not limited to, those set forth above when production capacity is high.

BRIEF SUMMARY OF THE INVENTION

In one embodiment, the present invention relates to a separations apparatus having a rectification section; a stripping section having at least one stripping tray in which the stripping tray extends across the cross-sectional area of the column and has a tray cross-sectional area and open areas through which vapor may pass, wherein each of the open areas has an open cross-sectional area, and wherein the sum of all of the open cross-sectional areas has a value in the range of from about 5% to about 50% of the tray cross-sectional area. The stripping tray produces a tray pressure drop during operation of the apparatus and the tray pressure drop is in a range of from about 1 mm Hg (0.02 psi) to about 10 mm Hg (0.2 psi) and the stripping tray has a tray efficiency during operation of the column which is equal to or greater than 20%. The apparatus may have a first stripping tray and a second stripping tray, wherein the first stripping tray and the second stripping tray are separated by a vertical distance that is at least 8 inches. It is not necessary for a stripping tray to have a downcomer.

The present invention may be used in one embodiment to purify acrylic acid and may produce a bottoms stream having acrylic acid in a concentration of greater than 50 wt %.

The present invention can be achieved though retrofitting an existing distillation column by replacing at least two trays in the stripping section with a single tray capable of producing a tray pressure drop during the operation of the apparatus in the range of about 4 mmHg (0.08 psi) to about 6 mmHg (0.12 psi).

In yet another embodiment, the present invention may have a distillation column having a feed inlet, an overhead outlet, a bottoms outlet, a reflux inlet and a reboiler return inlet, the column also has a column internal cross-sectional area bounded by an internal column diameter. The distillation column may house a rectification section located above the feed inlet and a stripping section located below the feed inlet.

The present invention may have a distillation column with a wall having an internal surface defined by the internal column diameter wherein the open areas allow vapor to flow through at a sufficient velocity to entrain a liquid present on the surface of at least one stripping tray providing liquid mass transfer such that the liquid contacts with the internal surface so as to wet the internal surface.

The present invention includes another embodiment having sufficient trays to provide 8 or more theoretical stages of separation, wherein the rectification section has sufficient rectification trays to provide at least 4 theoretical stages of separation and the stripping section has sufficient trays to provide at least 4 theoretical stages of separation.

Any of the embodiments of the present invention may be utilized to purify reactive and/or thermally unstable compounds. The present invention may produce an overhead stream having an acrylic acid composition of less than 10 wt %.

BRIEF DESCRIPTION OF THE DRAWINGS

FIG. 1 is a schematic illustration of a typical single column design of the present invention.

FIG. 2 is a schematic illustration of a typical dual-column design of the present invention.

FIG. 3 is a top view of one typical embodiment of a distillation tray of the present invention.

FIG. 4 is a side-view illustration of two trays under typical hydraulic operation in the present invention.

FIG. 5 is a side-view illustration of a temperature control tray of the invention.

DETAILED DESCRIPTION OF THE INVENTION

The present invention relates to the methods and apparati for the high capacity purification of thermally sensitive, unstable, or reactive compounds. The present invention includes a distillation process which utilizes fewer trays and provides high purity separations without requiring elevated temperatures or column pressures. The trays have an open area and a pressure drop designed to improve tray and column efficiencies and require fewer trays to reach desired product specifications.

The present invention includes the equipment for conducting separations, the processes for obtaining the desired product purity and methods of retrofitting existing columns to achieve the mechanical and/or performance parameters of the present invention.

These separation processes include but are not limited to continuous distillation, reactive distillation, azeotropic distillation, extractive distillation, multicomponent distillation, single and multiple flash distillation, vapor-liquid equilibrium processes, and any processes which utilize vapor liquid contact to effect mass transfer. The equipment can include vertical and horizontal pressure and vacuum vessels, reactors which effect separations, and heat exchange processes and equipment which provide for vapor-liquid contact and separations.

Throughout this specification and claims, unless otherwise indicated, references to percentages are by weight percent and all temperatures are in degrees centigrade. Unless otherwise specified, the endpoints of the ranges are considered to be approximated and to include other values that are within the knowledge of one of ordinary skill in the art to be insignificantly different from the respective endpoint (i.e. a value "about" or "close" or "near" to each respective endpoint). It is also to be understood that for purposes of this specification and claims that the range and ratio limits, recited herein, are combinable. For example, if ranges of 1-20 and 5-15 are recited for a particular parameter, it is understood that ranges of 1-5, 1-15, 5-20 or 15-20 are also contemplated. Also, the term "major amount" is understood to mean greater than 50 percent by weight of the total composition. The term "minor amount" is understood to mean less than 50 percent by weight of the total composition. The term "wastewater" is understood to mean any water stream having impurities, organic compounds and/or additives contained therein. In a like manner, the term "waste gas" is understood to mean a gas or mixture of gases having impurities and/or additives contained therein. The term "(meth)acrylic acid" is understood to encompass both acrylic acid and methacrylic acid. Likewise, the term "acrylic acid" is understood to encompass "(meth)acrylic acid" and related/like compounds. Similarly, "(meth)acrylonitrile" is understood to encompass both acrylonitrile and methacrylonitrile. The recitation "methacrylonitrile" encompasses acrylonitrile and the reverse is also true. "(Methyl)styrene" follows the same pattern. "(Methyl)styrene" encompasses both styrene and methylstyrene. The recitation "styrene" encompasses methylstyrene and the reverse is also true. Unless otherwise stated, ppm values are by weight. The term "froth height" and "liquid level" are used synonymously. Unless otherwise specified, pressures are absolute.

The processes and equipment (apparati) of the present invention include all of the components required to execute the purification of a desired compound by liquid-vapor separations.

FIG. 1 is an illustration of a typical single column design embodiment (single column embodiment) of the present invention. The unit operations represented in FIG. 1 are: a distillation column (1), main/vent condenser (5), vacuum jets or other vacuum system (30), inter/after condenser (35), a gravity separator (10), a reflux pump (15), a distillate product pump (40), a reboiler (25), a reboiler circulator pump (20), a bottoms product pump (45). The distillation column includes a feed zone (2), a rectification section (3), and a stripping section (4).

The process illustrated in FIG. 1 includes a feed stream (100), which is fed to the distillation column (1) in feed zone (2). Vapors of the column rise through the rectification section (3), and liquids in the column fall through the stripping section (4). The distillation column (1) has an overheads outlet and the overheads stream (110) is fed to a main/vent condenser (5). Condensate from the main/vent condenser (5), form the condensed distillate (112), which is combined with solvent make up (150), and fed to the gravity separator (10). The condensed distillate (112) also contains jet condensate (113). The jet condensate (113) originates from stream (111) drawn through the vacuum jets (30), and fed to the inter/after condenser (35). The non-condensables are removed from the inter/after condenser (35) through a non-condensables vent stream (140). The liquids generated by the inter/after condenser (35) constitutes the jet condensate (113) which is mixed with the condensed distillate (112). The gravity separator (10) produces a reflux stream (116) that feeds the reflux pump (15) which provides reflux (120) to distillation column (1). The distillate stream (115) from the gravity separator (10) is fed to a distillate product pump (40) which produces the distillate product stream (130). The distillation column (1) also produces a bottoms stream (160) which feeds a reboiler circulator pump (20). The reboiler circulator pump (20), pumps the bottoms stream to a tee where that bottoms stream divides into a reboiler feed stream (161) and a bottoms product pump feed stream (162). The reboiler (25) generates the reboiler return stream (170). The bottoms product pump (45), pumps the bottoms product stream (180).

FIG. 2 illustrates a dual-column design embodiment (dual-column embodiment) also known as a split column design utilizing the present invention. In this embodiment, the rectification section and stripping section may be distributed to multiple columns or vessels. The practice of distillation or separations by dual or split column design, may include some or all of the equipment illustrated in FIG. 2. It also may include additional equipment not illustrated in FIG. 2 that is typically utilized in such processing.

The distillation vessel(s) (columns, towers, etc.) typically utilized in the present invention have an internal diameter, an internal cross-sectional area, a column wall with a thickness and an outer diameter, distillation trays, optional packing (or other means to promote vapor-liquid contact) and a variety of other internals. Accesses are typically provided for control equipment and maintenance. The column's bottom can include a bottoms pot with a hold-up volume and a bottoms outlet. FIGS. 3-5 illustrate typical column and tray configurations.

Typical distillation vessel(s) as illustrated in FIG. 1 may include the following sections or zones: feed zone (2) including a feed tray and internals; a rectification section (or rectification zone) (3); a stripping section (or stripping zone)

(4) below the feed inlet and a bottoms hold up or pot (6). These zones each have the ability to pass vapor in an upward direction and liquid in a downward direction.

The inventive concepts of the present invention may be applied to any diameter vessel. The embodiments include columns with diameters greater than 8 feet. Columns as large as 30 feet or greater in diameter may be used with this invention. A preferred column diameter is between 10 and 15 feet. The column of Example 3 has a diameter of 14 feet, 4 inches.

A distillation column typically receives a feed stream at a feed inlet normally located between the rectification and stripping sections. In one embodiment, the toluene water and toluene/acetic acid azeotropes are separated from acrylic acid in the rectification section. The toluene/water azeotrope and the toluene/acetic acid azeotrope and acetic acid are stripped from acrylic acid in the stripping section.

In the present invention, distillation trays (trays) are present in each of the rectification and stripping sections. Each tray, or each section, may be designed to different criteria (e.g., pressure drop, tray hydraulics) based upon the temperature, flow and composition profiles of the column or the conditions at each individual tray. Apart from the above, it is also common to have more than one tray, or all trays, designed to the same specifications. Trays in the rectification section are called rectification trays. Trays in the stripping section are called stripping trays.

FIG. 3 is a top view of a typical distillation tray. The tray includes both open areas, represented by holes, and solid areas. The hole (1000) is typical of the plurality of holes included on that tray. The sheet metal or other material forming the non-hole surface is indicated as the tray (1020). The tray has a diameter (1010).

FIG. 4 illustrates a typical column tray under operating conditions. FIG. 4 indicates an upper tray (2100), and a lower tray (2200). The illustration shows vapors indicated by arrows rising through the column, and also liquids indicated by separate arrows passing downward through the tray, down the column. The tray spacing (2040) is indicated between the upper tray (2100), and the lower tray (2200). The froth height (2000), is shown as having a liquid level upon the lower tray (2200). There is a transport of bulk liquid (2010) downward through the column. There is a transport of bulk vapor (2020), upward through the column. As the vapor rises through the holes or the open area, it creates jet streams that entrain liquid creating a spray (2030). The spray is shown to be generated above and throughout the froth and will wet the inside of the column diameter.

FIG. 5 is an illustration of a distillation tray having a liquid level and froth height (3300), on a lower tray (3200) in which the thermowell (3010) is located below the froth height (3300) in the liquid level. The liquid level on a tray may be less than or equal to the froth height (3300). The illustration also represents the liquid level (3300), as well as the height between the lower tray and the lower diameter of the thermowell. FIG. 5 also illustrates the thermowell clearance (3500), the column shell (3030) and well-distributed bulk liquid (3020) falling from an upper tray (3100).

While any type of tray may potentially be employed with this invention, Examples 1, 2 and 3 below disclose dualflow trays employed in both the rectification and stripping sections. Examples of other acceptable tray types include sieve trays, valve trays, chimney trays, trays with downcomers, also dumped, random and structured packing may be used. Other means of vapor-liquid contact may be employed.

The rectification section typically experiences less polymer formation and fouling than the stripping section and both trays and packing may be employed. In one embodiment, dualflow trays (are perforated plate trays w/no downcomers) are used. Thus, the vapor and liquid pass through the same hole openings.

The invention includes embodiments which employ higher pressure drop trays and increased tray spacing in the stripping section of the column. The trays include holes having a cross sectional area through which vapors may pass. In many trays both liquids and vapors (liquids and vapors are collectively "fluids") pass through the hole area. The open area of a tray is the sum total of all individual hole areas through which fluids may pass. The open area has an impact on the efficiency of mass transfer between vapor and liquid phases. Tray efficiency is the ratio of the required number of equilibrium (or theoretical) stages of separation desired to the actual number of trays which are required. The open area also affects the pressure drop that is experienced across a tray during operation of the column. Tray pressure drop (pressure drop) is the absolute value of the difference in pressure that exists between the two sides of a tray under operating conditions.

Hydraulic instability is reduced in this invention by the horizontal leveling (e.g., stabilizing or leveling froth height, liquid level) of the vapor/liquid loading on the tray deck of the bubbling area. Liquid leveling is achieved by lowering the percent hole area on the tray panels to reach a range from about 24% open area to a range of about 14% to 20% open area (see Examples 1, 2 and 3). The open area is designed to increase the liquid/vapor loading of the tray which results in increased pressure drop and increased tray efficiency. The invention achieves an elevated per tray pressure drop for these trays. The trays are designed from pressure drops on the lower range of about 1 mmHg (0.02 psi) to about 2 mmHg (0.04 psi) to those of a higher range of pressure drop of about 4 mmHg (0.08 psi) to 5 mmHg (0.1 psi) per tray. Higher and lower ranges of per tray pressure drop are also possible based on the design requirements for total column pressure drop, stream concentrations, operating conditions, etc. In Example 2, the per tray pressure drop is in the upper range from about 4 mmHg (0.08 psi) to about 6 mmHg (0.12 psi).

The implementation of higher pressure drop trays in the column reduces polymer formation and improves efficiency of separation. The higher pressure drop per tray allows for the production of bottoms product in which acetic acid concentrations are reduced from a typical value of 1200 ppm to 1500 ppm to a range of less than 500 ppm. Lower values for a given embodiment of an inventive tray design can also be achieved by varying the operating conditions and process streams of the column.

Trays having 1.0 inch holes and a percent hole area yielding the same pressure drop of 4-6 mmHg (0.08-0.12 psi) as trays having 0.5 inch holes, operated under the same vapor and liquid flow rates and a 16% hole area, accumulate less polymer. Typically the percent hole area is from about 16% to 18%. The utilization of 1 inch diameter hole trays exhibits 50% less polymer accumulation than an embodiment utilizing ½ inch hole diameter trays in the same service. In the first retrofit embodiment (see Examples), the polymer accumulation rate demonstrated by ½ inch holes was 3.0 ft.$^3$/day and the modification of the trays to have 1 inch diameter holes resulted in 1.5 ft.$^3$/day of polymer. This is a 50% reduction in polymer accumulation rate for these trays.

The trays of the invention are designed for increased vapor/liquid loading and improve vapor-liquid interaction, as well as wetting of the interior walls of the column. This is achieved by increasing the vapor velocity through the hole openings from 35 ft./sec. to 45 ft./sec. and the liquid loading from 20 gpm/ft$^2$ to 30 gpm/ft$^2$. The unit "gpm/ft$^{2}$" is calculated as volumetric flow/(tray cross-sectional area fractional hole area). This invention provides for purification while reducing polymer formation on the walls by increased wetting and exposure to the inhibitor of the liquid phase.

The tray modifications of the invention may increase tray hydraulic stability, liquid entrainment, and eliminate "dead spots" reducing polymer formation. Additionally, holes in the tray rings and clips of the triangular, cantilever design may also be used to help reduce polymer accumulation. Trays with 1 inch diameter holes accumulate less overall polymer than inventive trays with ½ inch diameter holes. The inventive trays employing higher pressure drop with 1 inch diameter holes perform with equal stability compared to the trays with ½ inch diameter holes.

The invention may utilize a dualflow tray in the stripping section with a percent flood of 50-98% and employs a pressure drop in a range of about 4 mmHg to about 6 mmHg (0.08 psi to 0.12 psi). Dualflow trays of the invention may have a typical range of about 50% to about 90% flood, or a more loaded range where vapor/liquid loads are between 80% and 98% of flood. The flood point is defined as the vapor velocity at which liquid flow downward through the column is ceased (flood velocity) resulting in excessive accumulation of liquid inside the column. Percent of flood is the percent of the velocity as compared to the flood velocity.

In one embodiment the pressure drop per tray is in a range of about 4 mmHg (0.08 psi) to about 5 mmHg (0.1 psi) and the percent flood of the trays is in a range from about 80% to about 90%. These tray requirements improve efficiency and fewer trays are required to achieve a desired pressure drop.

Currently in industry large diameter tray efficiencies of the stripping section are approximately of 5-10% efficient. The invention raises tray efficiencies to greater than about 20%. With this invention tray efficiencies in the range of 40-50% and higher may be achieved.

In the stripping and rectification sections, tray spacing generally is in a range of from about 8 inches to about 60 inches. Typical tray spacing is from 18 to 36 inches. Tray spacing is commonly 36 inches in embodiments of the present invention. Typically the trays have holes which range in diameter from about ½ to about 1½ inches. Trays with 1 inch diameter holes increase the froth height from 3 inches to 4 inches and increase the entrainment of fluid by a factor of 4 in comparison to ½ each hole diameter trays designed for the some pressure drop and percent flood. The holes of the trays do not have to be of the same diameter on a given tray or between trays.

In the present invention, the per tray pressure drop in the stripping section may be maintained in a range of about 3 mmHg (0.06 psi) to about 5 mmHg (0.1 psi), or about 4 mmHg (0.08 psi) to about 6 mmHg (0.12 psi).

The invention accommodates the minimum pressure drop requirements for the column and can maintain a bottoms temperature on the order of 109° C. (228° F.) and a total pressure drop of 130-150 mmHg (2.5 -2.9 psi). The overhead composition is set by the minimum boiling azeotropes and the percent excess toluene which is controlled indirectly by the % water overhead controller.

Where trays are removed or reduced in number, the per tray pressure drop is increased proportionally to achieve a desired pressure drop. For Example, 2 trays at 3 mmHg (0.06 psi) are comparable to 1 tray of the invention with a pressure drop of 6 mmHg (0.12 psi).

Changing the percent water in the overhead from 11.5% to 13.0 wt % reduces the required bottoms temperature by 1° C. (1.8° F.) or more. The control tray temperature is also employed to optimize the column's temperature and composition profile. The higher efficiency trays of the invention allow for better control when adjusting the control tray temperature. The acetic acid concentration in the bottoms stream responds predictably with changes in the control tray temperature.

The tray and column specifications of this invention may be applied to the rectification section as well as to the stripping section as discussed above. Depending on the vapor/liquid loading a smaller hole area may be required to achieve the same desired pressure drop. Further, the increase in capacity effected by the trays of the present invention decreased β-acryloxypropionic acid (AOPA; acrylic acid dimer) concentration by a range of 2 wt % to 3 wt % in the bottoms product (see Examples 1 and 2).

The percent flood of trays in the rectification section may be 50-98% and the pressure drop is from about 4 mmHg (0.08 psi) to about 6 mmHg (0.12 psi). A typical range for operating dualflow trays in the rectification section is from 50% to 90% of flood, or the trays may be more heavily loaded and operation in a range of 80% to 98% of flood. The percent hole area is 14-20%. A value of in a range of 14-17% is typical.

The run time of the inventive process and the related equipment typically ranges between 30 and 50 days. Shorter and longer run times are possible based upon the desired production capacity, and tolerance for variation in product specifications. The control tray temperatures typically range between 66° C. (151° F.) and 73° C. (163° F.). The bottoms product stream rate ranges between 30,000 and 60,000 lb/hr. The % water in the overheads stream (aqueous stream, aqueous distillate product stream) typically ranges from 10 to 13%. The total pressure drop of a continuous distillation column is found to be within the range of 130 mmHg to 150 mmHg (2.5-2.9 psi). The column operates with an overhead pressure in a range of 110 mmHg to 115 mmHg (2.1-2.2 psi). The temperature of the column bottoms ranges from 105° C. to 113° C. (221-235° F.). The rate of aqueous feed to the distillation column ranges from 40,000 to 70,000 lb/hr. The maximum aqueous feed rate to the column is greater than 70,000 lb/hr.

The concentration of water in the feed stream is in a range from 23% to 40%. The concentration of water may be between 27 wt % and 36 wt %. Acetic acid concentration in the feed to the column is in a range of 2-4 wt %. Typically the acetic acid concentration is between 2 wt % and wt 3%.

The acetic acid found in the bottoms product is typically below 5,000 ppm, desirably less than 2,000 ppm, and preferably in the range of 400 ppm to 1,300 ppm. Very low concentrations of acetic acid in the bottoms product, less than 800 ppm, below 500 ppm (see Example 3) and as low as 300 ppm can be achieved in the present invention. The AOPA in the bottoms is in a range of 5 wt % to 10 wt %, and is typically within a range of 4 wt % and 6 wt %, and may be between 4 wt % and 5 wt %. The acetic acid present in the aqueous distillate is between 1 wt % and 10 wt %. Typically acetic acid concentrations in the aqueous distillate are between 4.0 wt % and 8.0 wt %.

As set forth in Table 5 of Example 3, the invention includes an average control tray temperature of 66.3° C. (151° F.); an average bottoms product stream rate of 35,200 lb/hr; an overhead water concentration of 11.9 weight %; a total column pressure drop of 139 mmHg (2.7 psi); an overhead pressure of 110 mmHg (2.1 psi), a bottoms temperature of 112.2° C. (234° F.); an aqueous feed of 52,700 lb/hr. A water concentration in the feed of 34.7 wt %; an acetic acid concentration in the feed of 2.3 wt %; an acetic acid concentration in the bottoms of 463 ppm; an AOPA concentration in the bottoms of 6.7 weight %; and acrylic acid concentration in the aqueous distillate of 1.3 weight %.

The control of distillation is typically accomplished through the utilization of equipment including, but not limited to, temperature, pressure and flow sensors in conjunction with data processing equipment and control valves. There are many column control methods and equipment utilized to achieve column control. Control systems may include any typical components to communicate operational data and effect changes in operating condition, such as computers, programmable logic controllers, gauges, sensors, etc.

In one embodiment of the invention the control system is set to monitor variables including the % water in the overhead stream and the control tray temperature average. The present invention may be utilized with any control system which can control a separations process.

The % water overhead controller is used to set the azeotrope composition in the overheads. At 110 mmHg (2.1 psi) absolute pressure, toluene forms a minimum boiling azeotrope 39° C. (102° F.) with water at approximately 85 wt % toluene/15 wt % water. Toluene also forms minimum boiling azeotrope 52° C. (126° F.) with acetic acid at approximately 79 wt % toluene/21 wt % acetic acid. In one embodiment the inventive column is typically run with 15-30% excess toluene (than is needed to theoretically meet the azeotrope compositions) to assure that the azeotropes for water and acetic acid are met. A typical range for this invention is from about 11.5 wt % water overhead to about 13 wt %. For a given rate, running at higher % water overhead also decreases the liquid/vapor loading in the upper section of the column and lowers the overall column pressure drop and bottoms temperature.

The present invention includes the installation of hydraulically stable trays as the temperature control trays (see FIG. 5). A hydraulically stable tray is one which is designed and operates at a pressure drop of 4-6 mmHg (0.8-0.12 psi) and the tray operates with even liquid distribution on the tray. This ensures that the thermowells in which the averaging thermocouples are housed are always submerged. Where both thermocouples are not submerged or where there is hydraulic instability, correct temperature control is difficult. Control trays may be located so as to bracket any temperature sensitive or temperature/separation controlling point of the column. Points selected for location of control trays may be chosen because they are in a sensitive region in which temperature change is related to key component separations.

The present invention provides improved process control. Adjusting the control tray temperature now allows the accurate control of the acetic acid concentration in the bottoms product. Increasing the control tray temperature pushes the acetic acid peak further up the column thus providing more stages for the separation between acetic acid and arylic acid, the result is a decrease in the acetic acid concentration in the bottoms product. Lowering the control tray temperature, allows the acetic acid concentration to increase in the bottoms product. Utilization of the trays of the present invention lowered the required control tray temperature and improved the control responsiveness for the column.

In one embodiment of the invention the variability in temperature control which range as high at +/−10° C. (18° F.) was determined to be within the range of +/− about 1° C. (1.8° F.) to about 3° C. (5.4° F.). Temperature control ranges of less than +/−1° C. (1.8° F.) are included in this invention.

It is also possible to achieve the design of the present invention by retrofitting an existing process or distillation system. (See Example 3)

An existing or designed column may be re-trayed and the operating conditions may be modified to achieve the elements of the instant invention. For example, the column may be re-trayed and the pressure, temperature and composition profile of the column may be changed. Where problems such as polymerization, or product quality and/or oscillation is observed, column process design characteristics may be changed. For example, the feed inlet may be elevated to a higher location in the column. This action will reduce the number of theoretical stages in the rectification section and change the operating line of the column. It will also increase the number of theoretical stages in the stripping section. Apart from moving the feed stream, reflux ratios as well as overhead and bottoms temperatures may be altered. The operating temperature of the condenser may be changed and the operating temperature of the reboiler may be changed. It is also possible to modify the feed of inhibitor and the activator of the inhibitor to the column.

The invention may be achieved by replacing trays in both the rectification and stripping sections of the column. Once the overall pressure drop for the column is established and the desired pressure drop for the rectification section and the pressure drop for the stripping section are determined, then these sections may be re-trayed to achieve the desired pressure drop while lowering the total number of trays and increasing each individual trays pressure drop so that the total pressure drop for each section whether rectification or stripping is equivalent to the design criteria. Tray modifications that will increase pressure drop and improve the efficiency of the trays include modification of the percent hole area, tray leveling, and tray loading. Changes in the operating conditions such as increasing the reflux ratio will also increase liquid loadings on the trays.

By modifying the trays as discussed above, each tray will have a greater pressure drop individually, however, the number of trays required to provide the desired pressure drop for either of the rectification or stripping section will be fewer. Thus, because there will be fewer trays required in the retrofitted column to achieve a design pressure drop in each identified section, the tray spacing may be increased.

One aspect of the invention is that the wetting of the column wall is increased by these modifications. Reducing hole area raises the vapor velocity and liquid level (froth height) on the tray. Raising the liquid level and reducing the hole area increases the vapor velocity through the tray. This increase in vapor velocity through a thicker layer of liquid hold-up on the tray will increase tray liquid turbulence and jet flow velocity. The integral result of all of these fluid dynamic changes is an improvement in tray efficiency and the wetting of the column wall which reduces polymerization. An aspect of the invention is the addition of a polymerization inhibitor (inhibitor) to the process. This inhibitor is found in the liquid hold-up of each tray and the wetting of the column wall will include the presence of the inhibitor at the column wall thereby additionally reducing polymerization.

Therefore this aspect of the invention may be achieved by taking an existing separation process, apparatus, or preferably distillation column and modifying the unit operations to achieve the elements of the invention and obtain the benefits of more efficient separation, increased capacity, longer runtimes and predictable operations.

In the second retrofit embodiment, a series of 2 trays were replaced among 20 trays in the rectification section of the column. The acrylic acid concentration of the aqueous distillate (aqueous distillate overhead, overheads stream) was reduced. A column which was typically operating at 4 to 5 wt % acrylic acid in the aqueous distillate was reduced to 1½ wt % acrylic acid concentration in the aqueous distillate. A typical range for the acrylic acid concentration in the aqueous distillate stream for the present invention is in a range from about 1 to about 2 wt % (see Example 2).

Also in the second retrofit embodiment, 4 inventive trays (2 trays in addition to those of the paragraph above) were installed to stabilize the hydraulics of the temperature control trays. The trays containing the thermocouples and the trays distributing liquid from above were included in the trays which were replaced. The trays below the feed trays (trays 43 and 45) had 17% hole area trays with 1 inch diameter holes installed. The trays above the feed try (trays 62 and 64) had 14% hole area with ½ inch diameter holes installed. Temperature control in a range of +/− about 1° C. (1.8° F.) to about +/−3° C. (5.4° F.) is typical of the invention.

The present invention includes not only the apparati involved in the purification of thermally unstable compounds but also includes the processes and conditions involved in producing streams which are enriched in such compounds. The equipment having the characteristics discussed above may be utilized to process many different types of feedstocks and to produce many types of product streams.

The inventive distillation process includes 8 or more theoretical stages (a theoretical stage or theoretical plate is defined to be a single vaporization step in which the liquid and vapors evolved from the liquid are in equilibrium). The rectification section has 4 or more theoretical stages and the stripping section also has 4 or more theoretical stages. In one embodiment, a distillation column is employed with 19 total theoretical stages, wherein the stripping section has 13 theoretical stages and the rectification section has 6 theoretical stages. Another embodiment has 25 total theoretical stages with 17 theoretical stages in the stripping section and 8 theoretical stages in the rectification section. In yet another embodiment there are 10 total theoretical with 7 theoretical stages in stripping section and 3 theoretical stages in the rectification section.

In one embodiment (see Example 3), an aqueous acrylic acid stream (feed steam, total feed stream, aqueous feed) is fed to a distillation column wherein it is subjected to azeotropic distillation in the presence of at least one distillation solvent to form a crude acrylic acid stream (acrylic acid stream, bottoms product stream). In acrylic acid service, a process for such purification employs continuous distillation. The distillation utilizes a distillation column and produces an aqueous distillate which is an acetic acid enriched stream (including other light end impurities and acrylic acid) and a bottoms stream of crude acrylic acid which is enriched in acrylic acid (see FIGS. 7 and 8). This invention may be practiced with any type of column having any desired internal means for vapor/liquid contacting. For instance, a sieve tray, a dual flow tray design, or a packed column may be used. The distillation column has a rectification section and a stripping section. The rectification section produces the overheads stream which is an aqueous distillate. The aqueous distillate (distillate) is passed through a gravity separator which separates the distillate product creating the distillate product stream (distillate product) and the organic reflux (reflux stream). The stripping section produces a bottoms stream which provides feed to the reboiler and a bottoms product stream (bottoms product). The reboiler feed is heated and the column receives thermal input via a reboiler return stream (reboiler return).

Typical components of the feed stream include, but are not limited, to one or more of water, propionic acid, acetic acid, benzaldehyde, protoanemonin, acrolein, acetaldehyde, methyl ether, methyl vinyl ketone, acetic acid, furfural, formaldehyde, propionaldehyde, maleic compounds including maleic acid and maleic acid anhydride, acrylic acid, β-acryloxypropionic acid (AOPA; acrylic acid dimer), formic acid and hydroquinone (and other inhibitors discussed further below).

Reactive and thermally unstable compounds are found in many classes of compounds and can be purified with the present invention. Compounds including, but not limited to, the following may be purified: alkanes and alcohols; alkenes; alkynes; aromatics; haloalkanes, ethers; epoxides; amines; aldehydes; ketones; carboxylic acids; esters; amides and nitrites. Example species from the above classes which may be purified with the invention include, but are not limited to octane, octene, pyrimidine, substituted aromatics, chloropentane, hexanol, diethylether, epichlorohydrin. Additional compounds which may be purified include acrylic acid, methacrylic acid, (meth)acrylate esters (e.g., methymethacrylate, ethyl acrylate, and butyl acryate), hydrogen cyanide, acrylonitrile, methacrylonitrile, styrene, methylstyrene, vinyl chloride, vinyl acetate, ethyl acetate, pthalic anhydride, maleic anhydride, ascorbic acid, and 3,5,5-trimethylcyclohexa-3en-1one. Olefins and aromatic compounds may also be purified. Other compounds include, but are not limited to, polymerizable vinyl monomers, large and small thermally sensitive molecules, biological molecules, pharmaceutical compounds, proteins, enzymes, acids, lipids, furfural, and olefinically-substituted aromatic compounds.

When the invention is utilized to purify acrylic acid, the feed composition to the distillation column has an acrylic acid concentration equal to or greater than about 40 wt %. Reactors to produce acrylic acid and/or acrolein, as well as catalysts and basic processing, generally known in the art and are described, e.g., in U.S. Pat. Nos. 4,203,906; 4,256,783; 4,365,087; 4,873,368; 5,161,605; 5,177,260; 5,198,578; 5,739,391; 5,821,390, and 6,384,274 B1 each of which are incorporated herein by reference. Patent documents EPA 1,070,700, EPA 1,106,598, EP 1,035,103 (A2) and U.S. Pat. No. 6,399,817 relate to acrylic acid purification and an each is incorporated herein by reference. In another embodiment, the feed stream has an acrylic acid composition of greater than about 60 wt %. Feed stream acrylic acid percentages may be as high as 80%. Typically acrylic acid concentrations in the feed stream range from about 40 wt % to about 80 wt %. The preferred embodiment utilizes a feed stream with acrylic acid in a range of about 65 wt % to about 70 wt % acrylic acid.

Acetic acid may also be present in the feed stream in a variety of ranges. Typically acetic acid is present in a range from about 1 wt % to about 5 wt %. In one embodiment the composition of acetic acid is in a range of about 2 wt % to about 4 wt %.

Water concentrations may vary widely in the feed stream. Typically water may be present in a composition greater than 25 wt %. However, lower values are also known. In one embodiment the water composition is present in a range from about 27 wt % to about 32 wt %.

Table 1 includes the feed compositions of the second retrofit embodiment of the present invention.

TABLE 1

Feed Composition Of the Second Retrofit Embodiment Of The Invention

| Component | Range | Typical Value |
|---|---|---|
| Water | 23-37 wt % | 30.5 wt % |
| Acetic Acid | 2-4 wt % | 2.5 wt % |
| Acrylic Acid | 60-70 wt % | 65.0 wt % |
| Hydroquinone (HQ, inhibitor) | 200-500 ppm | 325 ppm |
| Impurities: | | |
| Propionic Acid | | |
| Benzaldehyde | | |
| Acrolein | | |
| Furfural | | |
| Protoanemonin | | |
| Formaldehyde | | |
| Propionaldehyde | | |
| Maleics | | |
| AOPA | | |
| Formic Acid | | |
| Other | | |
| Total Impurities | 1-3 wt % | 2.0 wt % |

Feed stream flow rates for this invention are typically greater than 40,000 lb/hr, including greater than 50,000 lb/hr. The feed rate of one embodiment is 66,000 lb/hr (see Example 3). The upper end of the feed stream flow rates is not limited. Production rates of 100,000 lb/hr or greater are included in this invention.

In the invention, the feed enters the feed zone. Typically the rectification section is above the feed inlet and the stripping section below the feed inlet to the column.

The aqueous distillate may contain any compound which is fed to the distillation column. The aqueous distillate composition typically includes, but is not limited to water, benzaldehyde, acrolein, acetic acid, formaldehyde, propionaldehyde, acrylic acid, formic acid and toluene.

Where the invention is utilized in the purification of acrylic acid, the aqueous distillate is typically greater than 75 wt % water. Water concentrations of greater than 85 wt % are included. In one embodiment the concentration of water in the aqueous distillate ranges from about 85 wt % to about 95 wt %. Acetic acid is generally present in the aqueous distillate in concentrations less than 25 wt %. In one embodiment, the concentration of acetic acid is in a range of about 4 wt % to about 10 wt %. It is preferable to maintain the concentration of acrylic acid in the aqueous distillate at a relatively low concentration. Typically the concentration of acrylic acid is less than 10 wt % in the aqueous distillate. Concentrations of acrylic acid in the aqueous distillate of about 5 wt % or less are included. In one embodiment, the concentration of acrylic acid in the aqueous distillate is in a range from about 1 wt % to about 3 wt %. Toluene is also present in the aqueous distillate. Typically toluene constitutes less than 5% of the aqueous distillate. Toluene concentrations of less than about 1 wt % are included in the present invention. In one embodiment the toluene concentration of the aqueous distillate is in a range of about 0.05 wt % to about 0.2 wt %.

The overheads stream emanating from the top of the distillation column generally includes, but is not limited to, azeotropes of water, acetic acid, and/or acrylic acid with the distillation solvent. For instance, should toluene be utilized as a distillation solvent toluene/water, toluene/acetic acid, and toluene/acrylic acid azeotropes would be taken overhead in a two liquid phase system. The toluene/acrylic acid azeotrope is 99 wt % toluene/1 wt % acrylic acid, so theoretical losses of acrylic acid due to azeotrope formation as small. The overheads stream is phase separated into organic and aqueous phases. The phase separation may be done by any means known in the art.

In one embodiment, the condensed distillate is introduced into a tank and allowed to phase separate into an organic phase creating an organic stream and an aqueous phase creating an aqueous stream. The organic stream predominantly includes the distillation solvent. The aqueous stream includes, but is not limited to, acrylic acid, acetic acid, the distillation solvent and water. The organic stream is recycled back to the distillation column as a reflux stream. At least a portion of the aqueous stream may be recycled as wastewater.

Table 2 provides ranges and typical values for the aqueous distillate stream for the second retrofit embodiment of the invention.

TABLE 2

Aqueous Distillate Stream Composition For the Second Retrofit Embodiment Of The Present Invention

| Component | Range | Typical Value |
|---|---|---|
| Water | 85-94 wt % | 90.5 wt % |
| Acetic Acid | 4-8 wt % | 6.5 wt % |
| Acrylic Acid | 1-5 wt % | 1.5 wt % |
| Toluene | 200-1000 ppm | 400 ppm |
| Impurities: | | |
| Benzaldehyde | | |
| Acrolein | | |
| Formaldehyde | | |
| Propionaldehyde | | |
| Acrylic Acid | | |
| Formic Acid | | |
| Other | | |
| Total Impurities | 1-2 wt % | 1.5 wt % |

The distillation solvent or solvents of the present invention may be any solvent(s) suitable for the azeotropic distillation of a stream including acrylic acid. In one embodiment, the solvent is substantially water insoluble, generally having a solubility in water at room temperature of 0.5 wt % or less, preferably 0.2 wt % or less. Suitable examples of such a water insoluble solvent include, but are not limited to heptane; heptene; cycloheptane; cycloheptene; cycloheptatriene; methylcyclohexane; ethylcyclopentane; 1,2-dimethylcyclohexane; ethylcyclohexane; toluene; ethylbenzene; ortho-, meta-, or para-xylene; trichloroethylene; trichloropropene; 2,3-dichlorobutane; 1-chloropentane; 1-chlorohexane; and 1-chlorobenzene. In another embodiment, the solvent is selected from ethyl acetate, butyl acetate, dibutyl ether, hexane, heptane, ethyl methacrylate, diethyl ketone, methyl propyl ketone, methyl isobutyl ketone, and methyl tert-butyl ketone. In a further embodiment, the distillation solvent is a mixed solvent which includes at least two solvents. Suitable examples of solvents useful in such mixed solvent include, but are not limited to, diethyl ketone, methyl propyl ketone, methyl isobutyl ketone, methyl tert-butyl ketone, isopropyl acetate, n-propyl acetate, toluene, heptane and methylcyclohexane. The preferred distillation solvent includes toluene alone or in combination with any one or more other solvents.

The reflux stream may include any process compatible composition or solvent. Examples of these solvents include isopropyl acetate, toluene, methyl isobutyl ketone and combination thereof. The reflux stream typically contains toluene, water, acrolein, acetic acid, propionaldehyde, acrylic acid and formic acid.

In one embodiment, the reflux stream is predominantly toluene. Typically greater than 95% of the reflux is toluene. In one embodiment the concentration of toluene is in a range of about 98 wt % toluene to 99.5 wt % toluene. The reflux contains acrylic acid at a concentration generally of less than 5 wt %. Concentrations of less than 1% acrylic acid are included in the present invention. In one embodiment, the concentration of acrylic acid is in a range of about 0.2 wt % to about 0.6 wt %. Acetic acid is typically present in the reflux stream in concentrations of less than 5 wt %. Concentrations of less than 2.5 wt % or 1.0 wt % are included in the present invention. In one embodiment, the concentration of acetic acid is in a range from about 0.1 wt % to about 0.4 wt %. Water is typically present in the reflux stream in concentrations of less than 5 wt %. Concentrations of water less than 2.5 wt % are included. A 1.0 wt % concentration is included. In one embodiment, the concentration of water is in a range of 0.05 wt % to 0.1 wt %. In another, the range is from about 0.2 wt % to about 0.5 wt %. The reflux ratio (i.e., reflux rate/distillate product stream rate) is typically in a range of about 5.0 to 8.0. In one embodiment the reflux ratio is in a range of about 6.0 to 7.0.

Table 3 provides ranges and typical values for the reflux stream for the second retrofit embodiment of the invention.

TABLE 3

Reflux Stream Composition For the Second Retrofit Embodiment Of The Present Invention

| Component | Range | Typical Value |
|---|---|---|
| Toluene | 98.5-99.5 wt % | 99.1 wt % |
| Water | 0.2-0.5 wt % | 0.3 wt % |
| Acetic Acid | 0.1-0.4 wt % | 0.2 wt % |
| Acrylic Acid | 0.2-0.6 wt % | 0.3 wt % |
| Impurities: | | |
| Acrolein | | |
| Propionaldehyde | | |
| Formic Acid | | |
| Other | | |
| Total Impurities | 500-1500 ppm | 1000 ppm |

Generally, the crude acrylic acid stream (acrylic acid stream, bottoms product stream) has less than 1000 ppm, preferably less than 800 ppm, more preferably less than 500 ppm of water. The crude acrylic acid stream (acrylic acid stream, bottoms product stream) may also contain any one or a combination of the following: acetic acid, propionic acid, β-acryloxypropionic acid (AOPA), acrolein, furfural, benzaldehyde, maleic acid, maleic anhydride, protoanemonin, and acetaldehyde. The crude acrylic acid stream (acrylic acid stream, bottoms product stream) is generally sent to be used as a raw material in acrylic ester or acrylate polymer production. The acrylic acid may be used as is or be further processed, including but not limited to, additional distillation to remove specific impurities and further processing to form various grades of acrylic acid.

The bottoms stream of the invention may contain any component which is included in any stream that enters the column.

The bottoms stream typically contains water, propionic acid, benzaldehyde, acetic acid, furfural, protoanemonin, maleic acid compounds including maleic acid and maleic acid anhydride, acrylic acid, AOPA, hydroquinone and 4 hydroxy tempo (4 HT) inhibitor.

Where the invention is utilized for acrylic acid purification, the bottoms stream drawn from the stripping section of the column is typically greater than 75 wt % acrylic acid, however during start-up, shut-down and non-steady-state operation the bottoms concentration can vary dramatically, including ranges of 50 wt % or lower. Concentrations of acrylic acid greater than 85 wt % are included. In one embodiment, the concentration of acrylic acid in the bottoms product ranges from about 94 wt % to about 96 wt % (see Example 2). A range of 92 wt % to 96 wt % is included. Values greater than 96 wt % acrylic acid are possible by varying the concentrations of the acrylic acid in the feed stream, modifying reflux ratios or adding more theoretical stages to the distillation column. Acrylic acid dimer (AOPA) is also present in the bottoms product stream. Typically the AOPA concentration is less than 10 wt %, with typical values of less than 6 wt %. A preferred concentration of AOPA in the bottoms product is in a range from about 4 wt % to about 6 wt %. The bottoms product stream contains acetic acid in concentrations less than 2000 ppm. Concentrations less than 1500 ppm or 1000 ppm are included in this invention. Concentrations of acetic acid is in a range from about 300 ppm to about 1000 ppm are preferred. Acetic acid concentrations equal to or lower than 500 ppm are most preferred. Concentrations lower than 300 ppm are achievable by varying feed compositions, theoretical stages, reflux, etc. Water is also present in the bottoms product stream. Typically water is present in concentrations less than 2000 ppm. Water concentrations less than 1000 ppm are included in this invention. In one embodiment the product bottoms product stream concentration of water is in a range of about 100 ppm to about 300 ppm. The product bottoms product stream flow rate is in a range of from about 40,000 to 60,000 lb/hr with an average production of from about 40,000 to 50,000 lb/hr. A typical bottoms product stream flow rate is 46,000 lb/hr. In one embodiment acrylic acid is present in concentrations of about 94 wt % to about 96 wt % and the AOPA is reduced to a range of about 3 wt % to about 5 wt %.

The present invention includes the novel design and operation of the bottoms pot of the distillation column.

Higher production capacity and the resulting decreased residence time in the column bottoms allows AOPA reduction from a typical concentration in the range of 7 wt % or 8 wt % down to about 4 to about 5 wt % or less.

Table 4 provides ranges and typical values for the bottoms stream for the Second Retrofit embodiment of the invention.

TABLE 4

Bottoms Product Stream Composition For the Second Retrofit Embodiment Of The Present Invention

| Component | Range | Typical Value |
|---|---|---|
| Water | 100-1000 ppm | 300 ppm |
| Acetic Acid | 300-1000 ppm | 700 ppm |
| Acrylic Acid | 92-96 wt % | 93.6 wt % |
| AOPA | 3-6 wt % | 5 wt % |
| Hydroquinone | 10-50 ppm | 25 ppm |
| 4 Hydroxy-Tempo | 0.1-0.15 wt % | 0.11 wt % |
| Impurities: | | |
| Propionic Acid | | |
| Benzaldehyde | | |
| Furfural | | |
| Protoanemonin | | |

TABLE 4-continued

Bottoms Product Stream Composition For the Second Retrofit Embodiment Of The Present Invention

| Component | Range | Typical Value |
|---|---|---|
| Maleics | | |
| Other | | |
| Total Impurities | 0.9-1.7 wt % | 1.2 wt % |

Other compounds commonly found in the process stream of one embodiment include, but are not limited to formaldehyde, acrolein, and maleic compounds, as well as Fe, Mo and other typical contaminants found in chemical processing plants.

Inhibitor is added in the rectification section and optionally to the stripping section. Typically 50-90% of the inhibitor is fed with the reflux and the remaining inhibitor is fed with the aqueous feed stream. Generally, hydroquinone is present in the aqueous feed stream at a typical concentration of 325 ppm.

Polymerization inhibitors are useful to prevent polymerization both during the process of preparing and purifying thermally sensitive compounds including acrylic acid and (meth)acrylates and during their storage and shipment. In the second retrofit embodiment inhibitor is added to the column. Polymerization inhibitors may include those that are water soluble, alcohol soluble or organic soluble. Suitable examples include but are not limited to:

Hydroquinone (HQ); 4-methoxyphenol (MEHQ); 4-ethoxyphenol; 4-propoxyphenol; 4-butoxyphenol; 4-heptoxyphenol; hydroquinone monobenzylether; 1,2-dihydroxybenzene; 2-methoxyphenol; 2,5-dichlorohydroquinone; 2,5-di-tert-butylhydroquinone; 2-acetylhydroquinone; hydroquinone monobenzoate; 1,4-dimercaptobenzene; 1,2-dimercaptobenzene; 2,3,5-trimethylhydroquinone; 4-aminophenol; 2-aminophenol; 2-N,N-dimethylaminophenol; 2-mercaptophenol; 4-mercaptophenol; catechol monobutylether; 4-ethylaminophenol; 2,3-dihydroxyacetophenone; pyrogallol-1,2-dimethylether; 2-methylthiophenol; t-butyl catechol; di-tert-butylnitroxide; di-tert-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-dimethylamino-2,2,6,6-tetramethyl-piperidinyloxy; 4-amino-2,2,6,6-tetramethyl-piperidinyloxy; 4-ethanoloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; salts of 4-nitrosophenolate; 2-nitrosophenol; 4-nitrosophenol; copper dimethyldithiocarbamate; copper diethyldithiocarbamate; copper dibutyldithiocarbamate; copper salicylate; methylene blue; iron; phenothiazine (PTZ); 3-oxophenothiazine; 5-oxophenothiazine; phenothiazine dimer; 1,4-benzenediamine; N-(1,4-dimethylpentyl)-N'-phenyl-1,4-benzenediamine; N-(1,3-dimethylbutyl)-N'-phenyl-1,4-benzenediamine; N-nitrosophenyl hydroxylamine and salts thereof; nitric oxide; nitrosobenzene; p-benzoquinone; copper naphthenate; copper acetate; manganese dimethyldithiocarbamate; manganese diethyldithiocarbamate; manganese dibutyldithiocarbamate; manganese naphthenate; manganese acetate; manganese acetylacetonate; cobalt acetate; cobalt carbonate; cobalt acetate; nitrogen dioxide; nitrobenzene; nitrosobutane; N-nitrosodiphenylamine; diphenylphenylenediamine; nitrosocarbazole; 1-nitroso-2-naphthol; 2,4 dinitrobenzene; triphenyl phosphine; triethyl phosphine; tributyl phosphine; triphenyl phosphite; triethyl phosphite; Tri-i-propylphosphite; tributyl phosphite; tricyclohexyl phosphite; Soduim bisulfite; Butyl mercaptan; dodecyl mercaptan; N,N-diethylhydroxylamine; or isomers thereof; mixtures of two or more thereof; mixtures of one or more of the above with molecular oxygen. The inhibitor(s) may be used alone or combined with a suitable diluent. The polymerization inhibitor is typically used at levels ranging from 100 ppm to 4,000 ppm (based upon the total bottoms flow rate).

A vapor phase inhibitor such as n-phenyl hydroxylamine or derivatives thereof may be useful. Liquid phase inhibitors may also be useful. In a preferred embodiment, the vapor phase inhibitor is added to the reboiler and the bottom trays of the column, while the liquid phase inhibitor is added to the top and feed of the column. The amount of liquid phase inhibitor may range from 1 ppm to 1000 ppm, depending on the feed rate to the column.

Oxygen is common particularly in acrylic acid separation systems as a necessary component to work with the inhibitors like hydroquinone. Oxygen is added to the system to activate the inhibitors.

Another benefit of the invention is reduced waste loading. The aqueous distillate contains both acrylic and acetic acid, as well as solvent (toluene) and any other component that may entrained in the overhead stream. By increasing the tray and column efficiency in the present invention the ability to meet high purity specification in the acrylic acid bottoms product as well as a reduced overhead composition of acrylic acid reduces overall waste loading. The operational flexibility of the invention and the increased tray efficiencies allow for the product specification of acrylic acid to be raised and the overhead acrylic acid specification in the aqueous distillate waste to be reduced by as much as 80% or more.

The invention is not limited to the processes and equipment described above. The present invention may also be achieved through a dual column design as illustrated in FIG. 2. This embodiment includes the process design where rectification and stripping sections are distributed throughout separate columns.

FIG. 2 illustrates a first distillation section, a second distillation section, and a third distillation section. The first distillation section contains a first distillation column (500), a main/vent condenser (505), a gravity separator (510), a reflux pump (515), a product distillate pump (540), a first column reboiler circulator pump (520), a first column reboiler (525), and a first column bottoms pump (545). The first column bottoms pump feeds the second distillation column (600).

The first distillation column (500) is fed by a first column feed stream (5100). The first distillation column (500) produces a first column overheads stream (5110), which is fed to a first column main/vent condenser (505). The first column main/vent condenser (505) is connected to a first column vacuum system (506). The non-condensables leave the first column vacuum system (506) via the first column non-condensables stream (5111). The condensate is fed to a gravity separator (510) by the first column condensed distillate stream (5112). The first column condensed distillate stream (5112) receives solvent make-up (5150) prior to entering the gravity separator (510). The reflux from the gravity separator (510) is fed to the reflux pump (515). The reflux pump (515) provides the first column reflux stream (5120) to the first distillation column (500). The first distillation column (500) also produces a first column bottoms stream (5160) which is fed to the first column reboiler circulator pump (520). The first column reboiler circulator pump (520) produces a first column bottoms pump feed stream (5162) which splits to feed the first column reboiler (525) as a first column reboiler feed stream (5161). The first column reboiler (525) delivers the first column reboiler return stream (5170) to the first distillation column (500). The distillate product stream (5115) is pumped by the distillate product pump (540).

The first column bottoms pump (545), delivers feed to the second distillation column (600). This is the second column feed stream (6100). The second distillation column (600) produces a second column overheads stream (6110) which feeds a second column main/vent condenser (605), the second column non-condensables stream (6111) is removed by a second column vacuum system (606). The second column condensed distillate (6112) is delivered from the second column main/vent condenser (605) to a second column distillate receiver (610). The second column distillate receiver (610) provides a second column distillate stream (6113) which is fed to second column distillate pump (640), which provides the third column feed stream (7000) to the third distillation column (700). The second distillation column (600) also produces a second column bottoms stream (6160), the second column bottom stream (6160) is pumped by the second column reboiler circulator pump (620), and is split into a second column reboiler feed stream (6161) to second column reboiler (625), which provides the second column reboiler return stream (6170) to the second distillation column (600). The second column bottoms stream (6160) also produces the second column bottoms pump feed stream (6162) fed to the second column bottoms pump (645) which pumps the second column bottoms product stream (648).

Second column distillate pump (640) provides the third column feed stream (7000) to the third distillation column (700). The third distillation column produces a third column overheads stream (7110) which feeds the third column main/vent condenser (705). The third column main/vent condenser (705) produces a third column non-condensables stream (7111), which is drawn into the third column vacuum system (706). The third column main/vent condenser (705) also produces the third column condensed distillate (7162). The third column condensed distillate (7162) is fed to the third column distillate receiver (710). The third column distillate receiver (710) produces the third column distillate stream (7113), which is fed to the third column distillate pump (740) producing both the third column reflux (7120), and the third column product distillate stream (8100).

The third distillation column (700) also produces a third column bottoms stream (7160) which feeds the third column reboiler circulator pump (720). The third column reboiler circulator pump (720) pumps the third column bottoms stream (7160), which splits into the third column reboiler feed stream (7161), and the third column bottoms pump feed stream (7165). The third column bottoms pump feed stream (7165) is fed to the third column bottoms pump (615), which provides the second column reflux (7167) to the second distillation column (600). The third column reboiler feed stream (7161) is provided to the third column reboiler (725). The third column reboiler (725) provides the third column reboiler return stream (7170) to the third distillation column (700).

This invention will be described more specifically below with reference to the following, non-limiting, examples.

EXAMPLE 1

Acrylic acid was produced in accordance with the process diagram illustrated in FIG. 1. With reference to FIG. 1, acrylic acid-containing aqueous feed solution (100), azeotropic distillation column (1), azeotropic distillation column overhead vapor (110), condenser (5), aqueous-organic separator (10), azeotropic solvent containing reflux phase (120), aqueous containing distillate phase (130), azeotropic dehydration column bottoms (180).

Azeotropic distillation column (1), had the following physical characteristics:
1. 172 in. ID column
2. 71 dual-flow trays
3. Lower trays had 24% open area
4. Upper trays had 20% open area Acrylic acid-containing aqueous feed solution (63-67 wt % acrylic acid, 2-4 wt % acetic acid, 1-3 wt % impurities, and 26-34 wt % water) was fed to column (1). Overhead pressure in column (1) was set to 110 mmHg (2.1 psi) absolute and total pressure drop through the trays was held to 120 mmHg (2.3 psi) to minimize bottoms temperature which was 109° C. (228° F.). Pressure drop per tray was held to 1-2 mmHg (0.02-0.04 psi).

Bottoms product (180) contained: 92-94 wt % acrylic acid, 6-8 wt % acrylic acid dimer, and 0.1-0.2 wt % acetic acid. Aqueous distillate product (130) contained: 4-5 wt % acrylic acid, 6-8 wt % acetic acid, and 87-90 wt % water. Tray efficiencies for the 24% open area trays were less than 10%. Tray efficiencies for the 20% open area trays were 30%.

EXAMPLE 2

Azeotropic distillation column (1) had the following physical characteristics:
1. 172 in. ID column
2. 54 dual-flow trays
3. Lower trays had 16-18% open area
4. Upper trays had 14-20% open area Acrylic acid-containing aqueous feed solution (63-67 wt % acrylic acid, 2-4 wt % acetic acid, 1-3 wt % impurities, and 26-34 wt % water) was fed to column (1). Overhead pressure in column (1) was set to 110 mmHg (2.1 psi) and total pressure drop through the trays was allowed to rise to 140 mmHg (2.7 psi) resulting in a bottoms temperature of 111° C. (232° F.). Pressure drop per tray was increased to 4-6 mmHg (0.08-0.12 psi) by installing a plurality of lower open area trays in column (1).

Bottoms product (180) contained: 94-96 wt % acrylic acid, 4-6 wt % acrylic acid dimer, and 0.05-0.1 wt % acetic acid. Aqueous distillate product (130) contained: 1-2 wt % acrylic acid, 6-8 wt % acetic acid, and 90-93 wt % water. Tray efficiencies for the 16-18% open area trays were 40%. Tray efficiencies for the 14-17% open area trays were 50%. The embodiment of Example 2 achieved a 25% greater capacity than the embodiment of Example 1.

EXAMPLE 3

An existing acrylic acid column was retrofit (modified, revamped, retrofitted) to achieve a first retrofit embodiment and a second retrofit embodiment of the present invention. The "after retrofitting" column of table 5 contains the data of the Second Retrofit Embodiment. The operating data from before and after modification is found in the table below.

Column trays in this example are of the dual flow type. The initial modifications recently in the first retrofit embodiment were as follows: trays 3, 5, 7, 9, 11, 13, 15, 17, 19, 21, 23, 25, and 27 removed (71 original total trays). Installed 16.24% hole area tray panels (w/½" ID holes) on trays 2, 4, 6, 8, 10, 12, 14, 16, 18, 20, 22, and 24. Installed 20.00% hole area tray panel (w/½" ID holes) on tray 26.

The final modifications resulting in the second retrofit embodiment were as follows: Removed 16.24% hole area tray panels (w/½" ID holes) on trays 14, 16, 18, 20, 22, and 24 (72 original total trays). Installed 18.42% hole area tray panels (w/1" ID holes) on trays 14, 16, 18, 20, 22, and 24. Installed new tray on 27" spacing below tray 35 with 18.95% hole area tray panels (w/½" ID holes). This modification also reduced tray 34 spacing down to 33". Additional modifications related to tray support. These include: triangular/cantilever clip design w/1" scupper holes for clips 1, 8, 9, and 16; Tray 32 Ring—Installed triangular/cantilever clip design w/o 1" scupper holes for clips 1, 8, 9, and 16; Tray 33 Ring—Installed perpendicular clip design w/o 1" scupper holes for clips 1, 8, 9, and 16.

TABLE 5

Second Retrofit Embodiment Results

| Parameter | Before Retrofitting | After Second Retrofit |
|---|---|---|
| Control Tray Temp, ° C. (° F.) (Avg. Trays 43 & 62) | 72.1 (162) | 66.3 (151) |
| Crude Acrylic Acid Rate (CAA), lb/hr | 32,300 | 35,200 |
| H₂O Overhead, wt % | 11.2 | 11.9 |
| Total dP, mmHg (psi) | 117 (2.3) | 139 (2.7) |
| Overhead Press, mmHg (psi) | 112 (2.2) | 110 (2.1) |
| Bottoms Temp, ° C. (° F.) | 108.9 (228) | 112.2 (234) |
| Average Aqueous Feed, lb/hr | 49,900 | 52,700 |
| Total Feed, lb/hr | 51,100 | 56,100 |
| H₂O in Feed, wt % | 33.3 | 34.7 |
| acetic acid in Feed, wt % | 2.3 | 2.3 |
| acetic acid in Bottoms, ppm | 1,252 | 463 |
| AOPA in Bottoms, wt % | 6.7 | 6.7 |
| acrylic acid in Aqueous Dist, wt % | 5.0 | 1.3 |

Although the invention has been described in conjunction with a specific embodiment, many alternatives and variations will be apparent to those skilled in the art in light of this description and the annexed drawings. Accordingly, the invention is intended to embrace all of the alternatives and variations that fall within the spirit and scope of the appended claims. Further, the subject matters of the above-cited United States patents are incorporated herein by reference.

We claim:

1. A process for purifying a stream comprising at least one thermally sensitive compound, comprising the steps of:
    (a) providing a separation vessel having an internal diameter of greater than 8 feet, an internal cross-sectional area and at least one tray extending across said internal cross-sectional area;
    (b) providing said stream comprising at least one thermally sensitive compound to said separation vessel at a rate of at least 40,000 lb/hour, wherein said at least one thermally sensitive compound comprises (meth)acrylic acid and at least one other compound comprising acetic acid in an amount between 1 and 5 weight percent, based on the total weight of the stream; and
    (c) purifying said stream by operating said separation vessel and maintaining a pressure drop across at least one of said at least one tray in a range of between 1 mm Hg (0.02 psi) and 10 mm Hg (0.2 psi); and
    (d) producing a purified bottoms product stream comprising less than 10,000 parts per million acetic acid, based on the total weight of the stream.

2. The process according to claim 1, wherein said purifying step is achieved by operating said separation vessel and maintaining said pressure drop in a range of between 1 mm Hg (0.02 psi) and 6 mmHg (0.12 psi).

3. The process according to claim 1, wherein said at least one tray has at least one opening, said at least one opening having a diameter of greater than 25.0 millimeters.

4. The process according to claim 1, wherein said at least one tray is at least one type selected from the group consisting of: a dualflow tray, a sieve tray, a valve tray, a perforated plate tray, a chimney tray, a tray without a downcomer, and a tray with a downcomer.

* * * * *